US007478465B1

(12) United States Patent
Hamatake et al.

(10) Patent No.: US 7,478,465 B1
(45) Date of Patent: Jan. 20, 2009

(54) METHOD OF SECURING A RESTRAINING MEMBER ON A MEDICAL DEVICE

(75) Inventors: Bret Hamatake, Grantsville, UT (US); Daryl R. Edmiston, Sandy, UT (US); Karri L. Schlegal, Salt Lake City, UT (US); Steven W. Johnson, West Jordan, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 873 days.

(21) Appl. No.: 11/032,365

(22) Filed: Jan. 10, 2005

(51) Int. Cl.
*B23P 11/00* (2006.01)

(52) U.S. Cl. .............................. 29/428; 29/505; 29/235; 606/200

(58) Field of Classification Search .................. 29/428, 29/505, 235, 243.517, 244, 267, 270, 271, 29/272, 281.1, 281.5, 283.5, 284, 896.62; 606/200

See application file for complete search history.

(56) References Cited

U.S. PATENT DOCUMENTS

| 3,472,230 | A | 10/1969 | Fogarty |
| 3,592,186 | A | 7/1971 | Oster |
| 3,683,904 | A | 8/1972 | Forster |
| 3,889,657 | A | 6/1975 | Baumgarten |
| 3,952,747 | A | 4/1976 | Kimmell, Jr. |
| 3,996,938 | A | 12/1976 | Clark, III |
| 4,046,150 | A | 9/1977 | Schwartz et al. |
| 4,425,908 | A | 1/1984 | Simon |
| 4,447,227 | A | 5/1984 | Kotsanis |
| 4,580,568 | A | 4/1986 | Gianturco |
| 4,590,938 | A | 5/1986 | Segura et al. |
| 4,619,246 | A | 10/1986 | Molgaard-Nielsen et al. |
| 4,631,052 | A | 12/1986 | Kensey |
| 4,643,184 | A | 2/1987 | Mobin-Uddin |
| 4,650,466 | A | 3/1987 | Luther |
| 4,662,885 | A | 5/1987 | DiPisa, Jr. |
| 4,705,517 | A | 11/1987 | DiPisa, Jr. |

(Continued)

FOREIGN PATENT DOCUMENTS

DE          28 21 048       7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Jermie E Cozart
(74) *Attorney, Agent, or Firm*—Crompton, Seager & Tufte LLC (57) ABSTRACT

A stitching device and method of operating the stitching device to form an embolic protection device is disclosed. The stitching device includes a clamping assembly and an advancing assembly. The clamping assembly holds a restraining member about a filter assembly while the advancing assembly threads or stitches a securing member through the restraining member. The clamping assembly includes a first clamping portion and a second clamping portion, each having an upper row of teeth and a lower row of teeth divided by a channel. The advancing assembly includes a threading assembly with an engagement member for engaging and advancing the securing member.

12 Claims, 8 Drawing Sheets

U.S. PATENT DOCUMENTS

| | | |
|---|---|---|
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,886,061 A | 12/1989 | Fischelle et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Giffort, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |

| | | | | | | |
|---|---|---|---|---|---|---|
| 5,938,645 | A | 8/1999 | Gordon | EP | 0 411 118 A1 | 2/1991 |
| 5,941,869 | A | 8/1999 | Patterson et al. | EP | 0 427 429 A2 | 5/1991 |
| 5,941,896 | A | 8/1999 | Kerr | EP | 0 437 121 B1 | 7/1991 |
| 5,947,995 | A | 9/1999 | Samuels | EP | 0 472 334 A1 | 2/1992 |
| 5,951,585 | A | 9/1999 | Cathcart et al. | EP | 0 472 368 A2 | 2/1992 |
| 5,954,745 | A | 9/1999 | Gertler et al. | EP | 0 533 511 A1 | 3/1993 |
| 5,976,172 | A | 11/1999 | Homsma et al. | EP | 0 655 228 A1 | 11/1994 |
| 5,980,555 | A | 11/1999 | Barbut et al. | EP | 0 686 379 A2 | 6/1995 |
| 5,989,210 | A | 11/1999 | Morris et al. | EP | 0 696 447 A2 | 2/1996 |
| 5,989,271 | A | 11/1999 | Bonnette et al. | EP | 0 737 450 A1 | 10/1996 |
| 5,989,281 | A | 11/1999 | Barbut et al. | EP | 0 743 046 A1 | 11/1996 |
| 5,993,469 | A | 11/1999 | McKenzie et al. | EP | 0 759 287 A1 | 2/1997 |
| 5,997,557 | A | 12/1999 | Barbut et al. | EP | 0 771 549 A2 | 5/1997 |
| 6,001,118 | A | 12/1999 | Daniel et al. | EP | 0 784 988 A1 | 7/1997 |
| 6,007,557 | A | 12/1999 | Ambrisco et al. | EP | 0 852 132 A1 | 7/1998 |
| 6,010,522 | A | 1/2000 | Barbut et al. | FR | 2 580 504 | 10/1986 |
| 6,013,085 | A | 1/2000 | Howard | FR | 2 643 250 A1 | 8/1990 |
| 6,027,520 | A | 2/2000 | Tsugita et al. | FR | 2 666 980 | 3/1992 |
| 6,042,598 | A | 3/2000 | Tsugita et al. | FR | 2 768 326 A1 | 3/1999 |
| 6,051,014 | A | 4/2000 | Jang | GB | 2 020 557 B | 1/1983 |
| 6,051,015 | A | 4/2000 | Maahs | JP | 8-187294 A | 7/1996 |
| 6,053,932 | A | 4/2000 | Daniel et al. | SU | 764684 | 9/1980 |
| 6,059,814 | A | 5/2000 | Ladd | WO | WO 88/09683 | 12/1988 |
| 6,066,149 | A | 5/2000 | Samson et al. | WO | WO 92/03097 | 3/1992 |
| 6,066,158 | A | 5/2000 | Engelson et al. | WO | WO 94/14389 | 7/1994 |
| 6,068,645 | A | 5/2000 | Tu | WO | WO 94/24946 | 11/1994 |
| 6,086,605 | A | 7/2000 | Barbut et al. | WO | WO 96/01591 | 1/1996 |
| 6,117,154 | A | 9/2000 | Barbut et al. | WO | WO 96/04875 A1 | 2/1996 |
| 6,129,739 | A | 10/2000 | Khosravi | WO | WO 96/10375 | 4/1996 |
| 6,136,016 | A | 10/2000 | Barbut et al. | WO | WO 96/19941 | 7/1996 |
| 6,142,987 | A | 11/2000 | Tsugita | WO | WO 96/23441 | 8/1996 |
| 6,151,950 | A * | 11/2000 | Wilhelm et al. ......... 72/409.01 | WO | WO 96/33677 | 10/1996 |
| 6,152,946 | A | 11/2000 | Broome et al. | WO | WO 97/17100 | 5/1997 |
| 6,165,200 | A | 12/2000 | Tsugita et al. | WO | WO 97/27808 | 8/1997 |
| 6,168,579 | B1 | 1/2001 | Tsugita | WO | WO 97/42879 | 11/1997 |
| 6,171,327 | B1 | 1/2001 | Daniel et al. | WO | WO 98/02084 | 1/1998 |
| 6,171,328 | B1 | 1/2001 | Addis | WO | WO 98/02112 | 1/1998 |
| 6,179,851 | B1 | 1/2001 | Barbut et al. | WO | WO 98/23322 | 6/1998 |
| 6,179,859 | B1 | 1/2001 | Bates et al. | WO | WO 98/33443 | 8/1998 |
| 6,179,861 | B1 | 1/2001 | Khosravi et al. | WO | WO 98/34673 | 8/1998 |
| 6,203,561 | B1 | 3/2001 | Ramee et al. | WO | WO 98/36786 | 8/1998 |
| 6,206,868 | B1 | 3/2001 | Parodi | WO | WO 98/38920 | 9/1998 |
| 6,214,026 | B1 | 4/2001 | Lepak et al. | WO | WO 98/38929 | 9/1998 |
| 6,221,006 | B1 | 4/2001 | Dubrul et al. | WO | WO 98/39046 | 9/1998 |
| 6,224,620 | B1 | 5/2001 | Maahs | WO | WO 98/39053 | 9/1998 |
| 6,231,544 | B1 | 5/2001 | Tsugita et al. | WO | WO 98/46297 | 10/1998 |
| 6,235,044 | B1 | 5/2001 | Root et al. | WO | WO 98/47447 | 10/1998 |
| 6,235,045 | B1 | 5/2001 | Barbut et al. | WO | WO 98/49952 | 11/1998 |
| 6,238,412 | B1 | 5/2001 | Dubrul et al. | WO | WO 98/50103 | 11/1998 |
| 6,245,087 | B1 | 6/2001 | Addis | WO | WO 98/51237 | 11/1998 |
| 6,245,088 | B1 | 6/2001 | Lowery | WO | WO 98/55175 | 12/1998 |
| 6,245,089 | B1 | 6/2001 | Daniel et al. | WO | WO 99/09895 | 3/1999 |
| 6,258,115 | B1 | 7/2001 | Dubrul | WO | WO 99/22673 | 5/1999 |
| 6,264,663 | B1 | 7/2001 | Cano | WO | WO 99/23976 | 5/1999 |
| 6,264,672 | B1 | 7/2001 | Fisher | WO | WO 99/25252 | 5/1999 |
| 6,270,513 | B1 | 8/2001 | Tsugita et al. | WO | WO 99/30766 | 6/1999 |
| 6,277,138 | B1 | 8/2001 | Levinson et al. | WO | EP 0 934 729 | 8/1999 |
| 6,277,139 | B1 | 8/2001 | Levinson et al. | WO | WO 99/40964 | 8/1999 |
| 6,280,413 | B1 | 8/2001 | Clark et al. | WO | WO 99/42059 | 8/1999 |
| 6,287,321 | B1 | 9/2001 | Jang | WO | WO 99/44510 | 9/1999 |
| 6,290,710 | B1 | 9/2001 | Cryer et al. | WO | WO 99/44542 | 9/1999 |
| 6,309,399 | B1 | 10/2001 | Barbut et al. | WO | WO 99/55236 | 11/1999 |
| 6,319,268 | B1 | 11/2001 | Ambrisco et al. | WO | WO 99/58068 | 11/1999 |
| 6,344,049 | B1 | 2/2002 | Levinson et al. | WO | WO 00/07655 | 2/2000 |
| 6,640,412 | B2 * | 11/2003 | Iancea ..................... 29/505 | WO | WO 00/09054 | 2/2000 |
| 2001/0041909 | A1 * | 11/2001 | Tsugita et al. ............ 606/200 | WO | WO 00/16705 | 3/2000 |
| | | | | WO | WO 00/49970 | 8/2000 |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Athersclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120 (3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

METHOD OF SECURING A RESTRAINING MEMBER ON A MEDICAL DEVICE

BACKGROUND OF THE INVENTION

1. The Field of the Invention

The present invention generally relates to medical devices. More particularly, the present invention relates to mechanisms for selectively restraining medical devices and methods of manufacturing such mechanisms.

2. The Relevant Technology

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. These procedures can include angioplasty, atherectomy, and stenting. Unfortunately, such percutaneous interventional procedures, i.e., angioplasty, atherectomy, and stenting, often dislodge material from the vessel walls. This dislodged material can enter the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, kidneys, or brain, resulting in a stroke or infarction.

Some existing devices and technology use a medical device, such as an embolic protection device to limit or prevent the flow of dislodged material downstream from the occluded or blocked portion of the vessel. The existing technology includes balloon-type devices and filter-type devices. Balloon-type embolic protection devices include one or more balloons that can be inflated at a location distal to the occluded or blocked portion of the vessel. This type of device is useful in preventing the flow of dislodged material, but also prevents blood from flowing downstream. These balloon-type devices can only be used for a limited period of time; else the lack of blood flow to particular areas of the body may result in undesirable side effects, such as stroke, seizures, or the like.

In contrast, filter-type embolic protection devices usually include a filter that expands under the influence of one or more biased struts. The filter is formed from an organic or inorganic polymer film which includes pores or openings that allow the blood to pass while at the same time preventing larger debris from passing downstream. The filter-type device allows blood to flow downstream of the occluded or blocked portion of the vessel, which is an advance over the balloon-type devices. Unfortunately, there are significant problems associated with positioning the filter-type device prior to deployment to filter dislodged material.

The filter and struts of the filter-type device are usually compressed or restrained in some manner in order to be easily deployed within the vasculature of the patient. Usually, a catheter compresses or restrains the filter-type device. Locating the catheter at the occluded or blocked portion of the vessel occurs as a physician or clinician advances the catheter containing the filter along a guide wire positioned within the lumen of the patient. Positioning the catheter at a location for deploying the filter-type device requires passing the catheter through the occluded or blocked region of the vessel. Since the outside diameter of the catheter is far greater than the guide wire, moving the catheter past the occluded or blocked region of the vessel can dislodge embolic material. As mentioned above, this dislodged material can occlude smaller downstream vessels, potentially blocking blood flow to tissue and resulting in a stroke or infarction. Additionally, moving the catheter through the tortuous anatomy of the patient can damage portions of vessels and other body lumens; resulting in an increased probability of adverse procedural outcomes.

It is desirable to have a mechanism for restraining the filter and struts of a filter-type device which results in a smaller outside diameter than a catheter. By reducing the profile of the deployment mechanism, the possibility of dislodging materials during insertion of the filter-type device is reduced. In addition, because of the small and delicate nature of the filter assembly, it is desirable that the restraining mechanism be easily manufactured with as few and as simple of steps as possible.

BRIEF SUMMARY OF THE INVENTION

The present invention is directed to a stitching device usable to mount a mechanism for restraining a medical device, such as the expandable elements of an expandable-type embolic protection device. The present invention also relates to methods, processes, and techniques for creating the medical device and restraining expandable elements of the medical device.

The stitching device can generally include a clamping assembly and an advancing assembly which cooperate together to secure the restraining member around a portion of the medical device. Specifically, the clamping assembly holds the restraining member in place while the advancing assembly threads or stitches the securing member through the restraining member. The cooperation of the clamping assembly and advancing assembly thus provides a simple and efficient manner for inserting the securing member into and through portions of the restraining member.

In one embodiment, the restraining member can be a section of thin film generally having a first side, a second side, and an intermediate portion. The securing member, in one configuration, can be a thin wire threaded through the restraining member. A seam is thus formed between the first side and second side of the restraining member.

The clamping assembly and advancing assembly can be mounted on a single base or separate bases. They may also be mounted to other supporting structures. The clamping assembly includes a first clamping portion and a second clamping portion. The first and second clamping portions can be disposed on discreet bases which are disposed such that the first clamping portion and the second clamping portion can be selectively positioned between an open and a closed position.

One or both of the bases of the clamping portions can be slidably mounted to a base using one or more linear positioning systems. In one embodiment, a linear positioning system may be connected to the second clamping portion. The second clamping portion may be disposed on a carriage which may be slidably disposed on a slide. A micrometer can be disposed on the carriage to move the carriage along the slide in an incremental manner.

Each clamping portion may include an upper row of teeth and a lower row of teeth separated by a channel formed therebetween. This can be achieved by forming a row of teeth in the clamping portion and then drilling or machining a channel through the teeth to form a distinct upper row and lower row of teeth. Generally, the upper rows of teeth of the first clamping portion and second clamping portion are complementary. Similarly, the lower rows of teeth of the first clamping portion and second clamping portion are a complimentary. However, it will be appreciated that the rows of teeth need not be complimentary with respect to the first clamping portion and second clamping portion. Similarly, the size of the teeth of the upper row and lower row of each clamping portion are generally the same. However, it is not necessary that they be the same.

The first clamping portion and second clamping portion can be moved between an open position and closed position. The closed position occurs when the first clamping portion and the second clamping portion are brought close together sufficiently that a portion of the restraining member is held tightly by the first clamping portion and the second clamping portion. When the first clamping portion and second clamping portion are in the closed position, the channels formed in the first clamping portion and second clamping portion form a receiving channel. The receiving channel can have various shapes, for example, circular, oval, ovate, rectangular, or any shape which is conducive to the purposes for which the receiving channel is intended.

The first and second clamping portion each may include a trough portion which, when the clamping portions are in the closed position, cooperates to form a combined trough in which to receive a portion of the medical device. In addition, a gap is formed underneath the first clamping portion and second clamping portion under which a technician can access portions of the restraining device during assembly of the medical device.

Generally, a technician places the restraining member around a portion of the medical device and places the ends of the restraining member through the gap formed between the first clamping portion and second clamping portion. The technician then closes the clamping portions about the sides of the restraining member such that the complimentary teeth of the clamping portions form folds in the restraining member. Each fold generally has two contiguous segments with each segment having generally two layers of the restraining member material. Thus positioned, the receiving channel holds the folds of the restraining member stationary so that the securing member can be passed through the receiving channel through the folds of the restraining member.

Cooperating with the first clamping portion and the second clamping portion is an advancing assembly. The advancing assembly, which threads the securing member through the restraining member, includes a threading assembly disposed on a linear positioning system. The threading assembly can be disposed on a carriage, which in turn, can be disposed on a slide. A spacer block can be optionally disposed between the threading assembly and the linear positioning system to align the threading assembly vertically with the clamping assembly. The threading assembly can include a pair of guide blocks disposed on the spacer block. The guide blocks can cooperate to form a channel therebetween and can be collectively referred to as a guide block. This may be especially the case where the guide blocks and spacer block are formed integrally to have a channel formed therethrough.

The bottom surface of the channel includes a central groove and an offset groove. The central groove can be configured to receive a portion of the securing member while the offset groove can receive a portion of the guide member so that they do not cross or interfere with one another. The threading assembly can include an advancement head that can be slidably disposed on the guide block. The advancement head can include an engagement member extending downwardly into the channel of the guide block. In one embodiment, the engagement member is a vertical blade which is coupled to a first and second block, the blocks forming the advancement head. In addition, one or more spring washers may be disposed between the advancement head and the guide block which biases the advancement head upward so that the engagement member is disposed in the channel but suspended over the bottom surface of the channel.

When the securing member is disposed in the central groove of the channel, the engagement member can selectively engage and advance the securing member forward. The engagement member thus reinforces the length of the securing member so that it does not buckle under the pressure applied thereto. The movement of the threading assembly can be automated as appreciated by those skilled in the art. Furthermore, the movement of the threading assembly may be incremental or continuous.

The method of assembling the medical device using the stitching device includes wrapping the restraining member around a portion of the medical device such that the ends of the restraining member are hanging downward. The wrapped filter assembly is then placed in one of the troughs of one of the first and second clamping portions, if present, so that the opposing clamping portion can be brought into contact with the sides of the restraining member. The gap formed between the first clamping portion and second clamping portion allows the technician to reach therein with their fingers or a grasping tool and draw the sides of the restraining member downward into the gap until the clamping portion is sufficiently engaged with the restraining member. The clamping of the clamping assembly at the same time forms a plurality of folds in the restraining member.

A securing member is stitched or threaded through the folds of the restraining member through the receiving channel formed by the first clamping portion and second clamping portion. The securing member is first placed in the advancing assembly prior to, simultaneously with, or subsequent to clamping the restraining member in the clamping assembly. The secure member is placed in the central groove of the channel of the guide block and aligns with the receiving channel of the clamping assembly. The advancing assembly is then moved forward until the distal end of the securing member is centrally disposed in the receiving channel and contacts the first segment of the first fold. The threading assembly can then be operated to slowly advance the securing member through the folds of the restraining member. Opening the clamping assembly thus releases the medical device with the restraining member held together with the securing member.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE EXEMPLARY EMBODIMENTS

Generally, the invention relates to a mechanism for restraining a medical device, such as, but not limited to, an expandable medical device. The following discussion is directed to a mechanism for restraining the filter and struts of a filter-type embolic protection device. The following discussion also generally relates to the methods, processes and techniques for creating such an embolic protection device and restraining its filter and struts. Although reference is made to the mechanism for restraining the filter and struts of a filter-type device and also the methods, processes and techniques for creating such embolic protection device, one skilled in the art will understand that the present invention can be more generally associated with a variety of other types of medical device, whether or not such are expandable or usable for embolic protection. For instance, and not by way of limitation, the present invention can apply to and be used with stents, grafts, vena cava filters, detachable embolic coils, any radially expandable medical device, or any detachable medical device.

Figure 1:
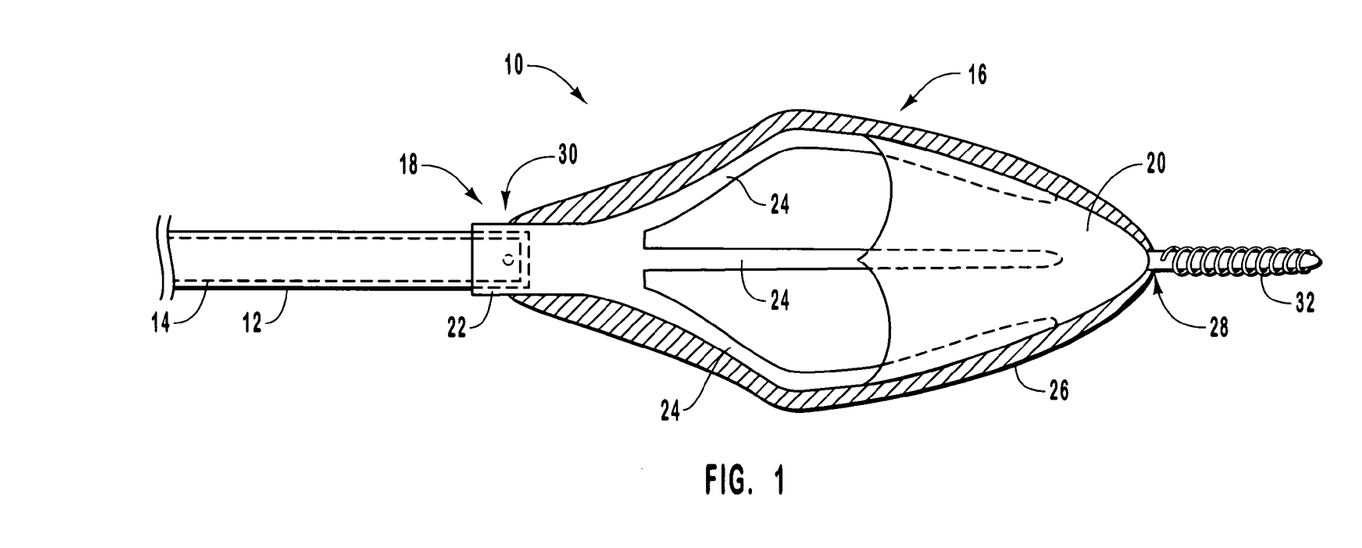
FIG. 1 illustrates the distal end of an exemplary embolic protection device for which apparatuses according to the present invention may be used to assemble.

With reference to FIG. 1, illustrated is an exemplary medical device, such as an embolic protection device 10 in a deployed configuration. Embolic protection device 10 can include a guide member 12 having an optional lumen 14 extending between the distal end and the proximal end of the guide member 12. A filter assembly 16 mounts to the distal end of guide member 12. This filter assembly 16 includes a filter basket 18 supporting a filter 20. The filter basket 18 attaches to the distal end of guide member 12 by way of a body 22, while a plurality of struts 24 support filter 20. Each strut 24 can be biased to move outwardly from the longitudinal axis of guide member 12 when deploying filter 20.

Figure 2:
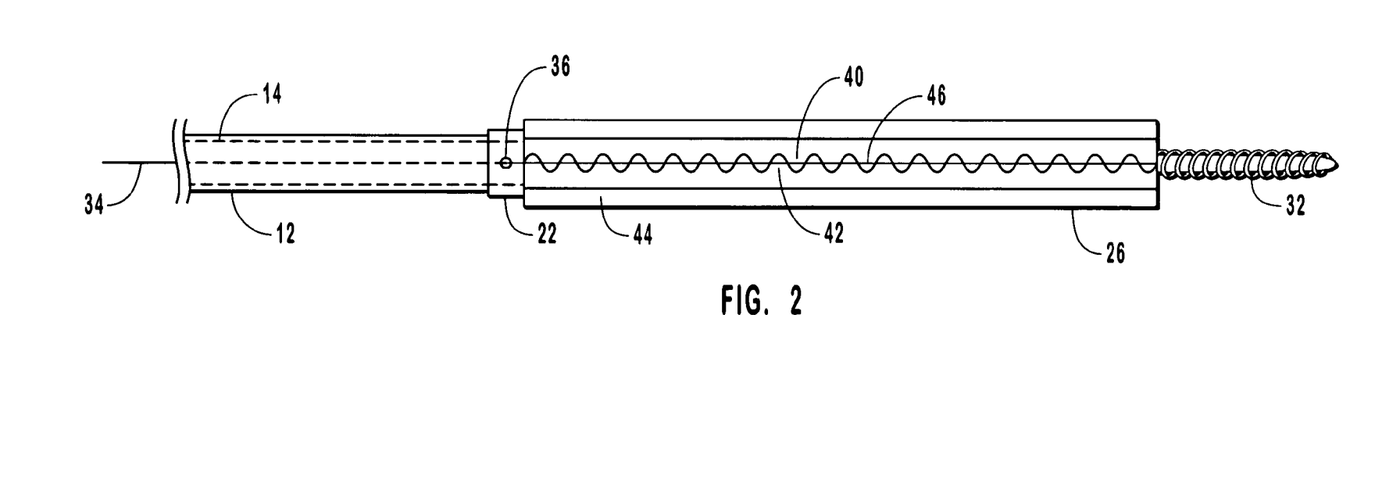
FIG. 2 illustrates the embolic protection device of FIG. 1 in the restrained position.

To maintain filter assembly 16 in a closed position with the struts 24 restrained and prevented from moving outwardly, a restraining member 26 surrounds filter assembly 16. Restraining member 26 applies a force against struts 24 to prevent the struts from extending outwardly. FIG. 1 illustrates restraining member 26 upon deploying filter 20, while FIG. 2 shows restraining member 26 applying the restraining force upon struts 24 and filter 20. With continued reference to FIG. 1, at least one of a distal end 28 and a proximal end 30 of restraining member 26 attaches to filter assembly 16. The distal end 28 can attach to one of struts 28 or to a tip 32 extending from body 22, tip 32 optionally including an atraumatic portion and a coil surrounding at least a portion of tip 32. Other configurations of tip 32 are known to those skilled in the art.

With reference now to FIG. 2, to maintain the restraining force upon struts 24 (FIG. 1), a securing member 34 cooperates with restraining member 26. In the illustrated configuration, securing member 34 stitches or passes through restraining member 26. This securing member 34 passes through an aperture 36 in body 22 and extends toward the proximal end of guide member 12 through lumen 14.

Restraining member 26 may be a section of thin film wrapped around filter 20 and struts 24. Restraining member 26 includes a first side 40 and a second side 42 separated by an intermediate portion 44. Restraining member 26 surrounds filter assembly 16 in such a manner that portions of intermediate portion 44 contacts with, are juxtaposed to, are contiguous with, or are adjacent one to another. Alternatively, because intermediate portion 44 is contiguous with the first side 40 and second side 42, a first side 40 can be contacting, juxtaposed, contiguous, or adjacent to second side 42 or intermediate portion 44. The section of restraining member 26 may have a generally polygonal configuration. However, restraining member 26 can have various other configurations so long as it is capable of performing the functions described herein.

In FIG. 2, a thin wire forms securing member 34. Securing member 34 passes through such portions of intermediate portion 44 and/or sides 40, 42 to secure restraining member 26 upon filter assembly 16. A seam 46 is thus formed with the restraining member 26. To further aid with applying a restraining force against struts 24, first side 40 and second side 42 may be folded to attach to respective portions of the outside surface of restraining member 26.

To release restraining member 26, a proximal end (not shown) of securing member 34 extends to a proximal end (not shown) of guide member 12, either within or without lumen 14 of the guide member. A physician or clinician pulling the proximal end (not shown) in a proximal direction moves securing member 34 proximally and longitudinally. This causes removal of securing member 34 from at least a portion of restraining member 26, with a resultant release of the restraining force applied by the restraining member. This allows struts 24 to extend outwardly and filter 20 to deploy.

The thin film of restraining member 26 may be constructed of any desired material which has a sufficiently small thickness, high tensile strength, high tear strength, and degree of elasticity. Optionally, an elastomeric material forms restraining member 26. Using the elastomeric material enables bending of restraining member 26 while embolic protection device 10 passes through the contours of the vascular system of a patient and enables straightening of embolic protection device 10 through the straight portions of the vascular system.

In another configuration, restraining member 26 can be constructed of the same material as filter 20, but may need to be constructed thicker because of the restraining function required of restraining member 26. For instance, the material can be one of a variety of polymer or silicone plastics, such as but not limited to, heat shrink plastic, organic and inorganic polymers, low-density polyethylene (LDPE), polyethylene terphthalate (PET), polytetrafluoroethylene (PTFE), fluorinated ethylene propylene (FEP), polyethylene (PE), or polyurethane (PU). In one embodiment, restraining member 26 is a polyurethane material having a thickness of about 12μ to about 18μ. In some configurations, restraining member 26 can be radiopaque or include one or more radiopaque markers.

Securing member 34 can be formed from a variety of different materials, so long as the material used is sufficiently strong to allow the securing function and actuating movement disclosed herein without breaking securing member 34. For example, securing member 34 can be fabricated from plastics, polymers, metals, composites, alloys, synthetic materials, combinations thereof, or other material that is capable of performing the function of being disposed through restraining member 26 and capable of being withdrawn therefrom.

Filter assembly 16 disclosed herein is described in further detail in U.S. patent application Ser. No. 10/186,275, filed Jun. 28, 2002, entitled "Methods, systems and devices for providing embolic protection and removing embolic material" and U.S. patent application Ser. No. 10/290,099, filed Nov. 7, 2002 and entitled "Methods, systems and devices for delivering stents," which applications are incorporated herein by reference.

Figure 3:
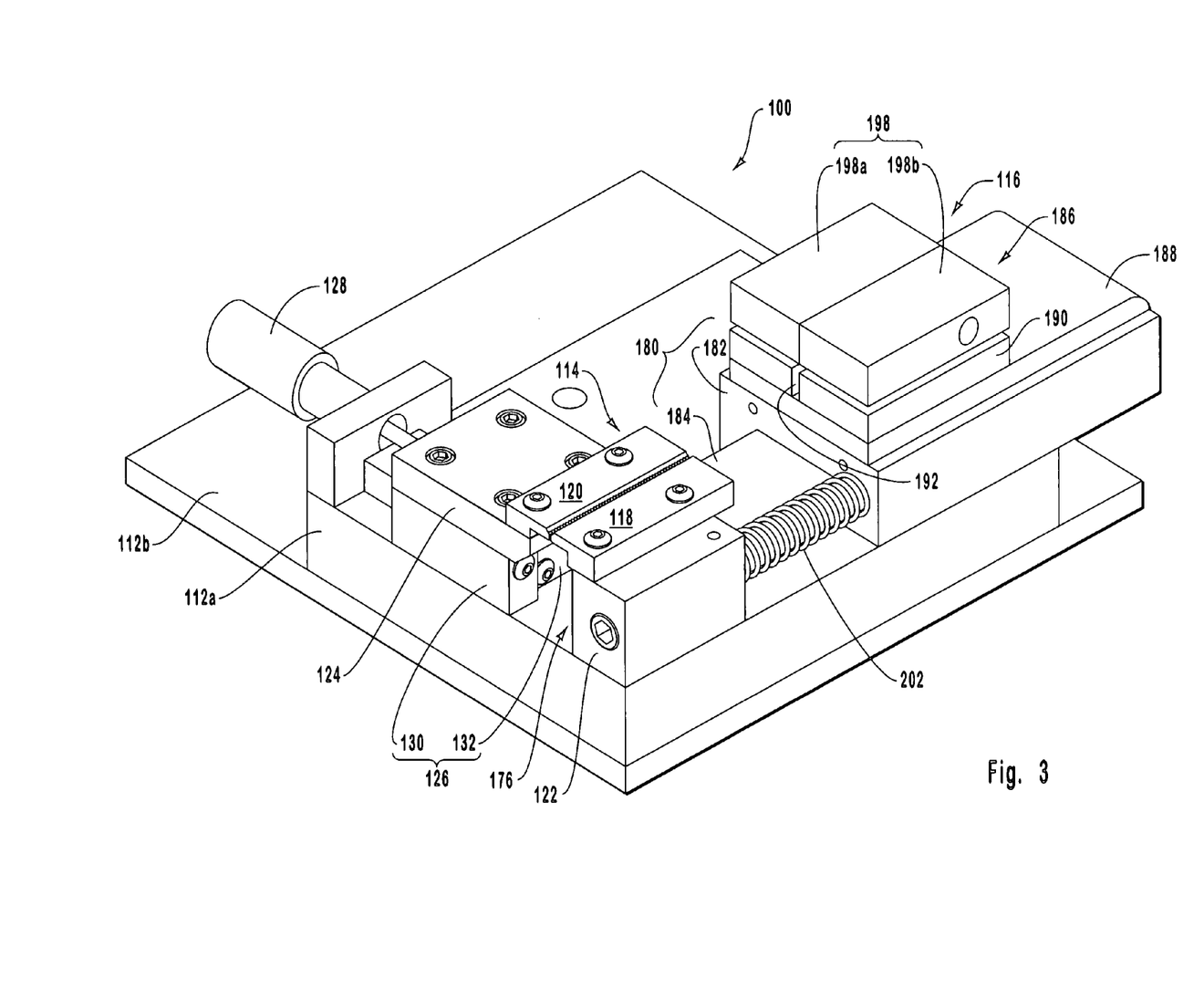
FIG. 3 illustrates a perspective view of a stitching device according to one embodiment of the present invention.

Turning now to FIG. 3, because of the small and delicate nature of restraining member 26 and securing member 34, a stitching device 100 is provided to assist in assembling embolic protection device 10. By way of overview of stitching device 100, the stitching device includes a base 112a upon which are mounted a clamping assembly 114 and an advancing assembly 116. Clamping assembly 114 and advancing assembly 116 cooperate together to secure restraining member 26 (FIG. 2) around the packed filter assembly 16 (FIG. 2). Specifically, clamping assembly 114 holds restraining member 26 (FIG. 2) in place while advancing assembly 116 threads or stitches securing member 34 (FIG. 2) through restraining member 26 (FIG. 2). The cooperation of clamping assembly 114 and advancing assembly 116 provides a simple and efficient manner for inserting securing member 34 into and through portions of restraining member 26.

Optionally, base 112a can be mounted on a second base 112b, which can, in turn, be mounted to various support structures. Such support structures may include, but are not limited to, legs, feet, other pedestal-like structures, or other structures capable of supporting stitching device 100. In addition, while FIG. 3 shows clamping assembly 114 and advancing assembly 116 sharing a common base 112a, they need not share the same base.

With continued reference to FIG. 3, clamping assembly 114 includes a first clamping portion 118 and a second clamping portion 120. The first and second clamping portions 118, 120 aid with holding restraining member 26 during insertion of securing member 34. As shown, first clamping portion 118 mounts on a first clamping base 122, which attaches to base 112a. Similarly, second clamping portion 120 mounts on a second clamping base 124. The second clamping base 124, however, moves relative to first clamping base 122 to selectively position first clamping portion 118 and the second clamping portion 120 between an open and a closed position. Although FIG. 3 illustrates clamping portion 118 and clamping base 122 as discreet members they may be formed as a single integral member. This is also true for clamping portion 120 and clamping base 124.

As used herein, the term "closed position" refers to where the first and second clamping portions 118, 120 are each contacting at least a portion of restraining member 26. Alternatively, the term "closed position" refers to where the first and second clamping portions 118, 120 have at least a portion thereof contacting at least a portion the opposing clamping portion. The term "open position" refers to where at least one of or both of the first and second clamping portions 118, 120 are not contacting at least a portion of restraining member 26. Alternatively, the term "open-position" refers to where first and second clamping portions 118, 120 do not touch each other and where a portion of restraining member is not disposed between the clamping portions.

To make second clamping portion 120 moveable, second clamping base 124 mounts to a linear positioning system 126, such as a linear translator, linear stage, or linear positioning device. This linear positioning system 126 provides accurate linear movement of second clamping portion 120 relative to first clamping portion 118. Illustratively, linear positioning system 126 includes a manual micrometer 128 that can be rotated to accurately move a carriage 130 of linear positioning system 126 along a linear slide 132 that functions as a linear bearing and a guide. In the illustrated configuration, manual rotation of micrometer 128 advances second clamping portion 120 toward first clamping portion 118. In this manner, first clamping portion 118 and second clamping portion 120 can be selectively positioned between a closed position and an open position.

Optionally, linear slide 132 can include one of a variety of different linear bearings, such as but not limited to, air, flat ball cage, ball spline, ball busing, needle roller cage, cam follower, crossed roller, guide wheel, hydrostatic, plain or journal, linear motion guide, flat roller cage, or linear rollers. Other configurations of linear positioning system 126 can include digital micrometers, fine screws, differential screws, automated controllers or other structures to move carriage 130 along linear slide 132.

Although reference is made to first clamping portion 118 being fixed and second clamping portion 120 being moveable, one will understand that both first clamping base 122 and second clamping base 124 can be slidably disposed on base 112. The movement of one or both of first clamping base 122 and second clamping base 124 can be optionally automatically operated by appropriate computer control and associated circuitry. However, micrometer slide 128 may be preferred where it is desirable to be able to incrementally close first clamping portion 118 and second clamping portion 120 together.

Figure 4:
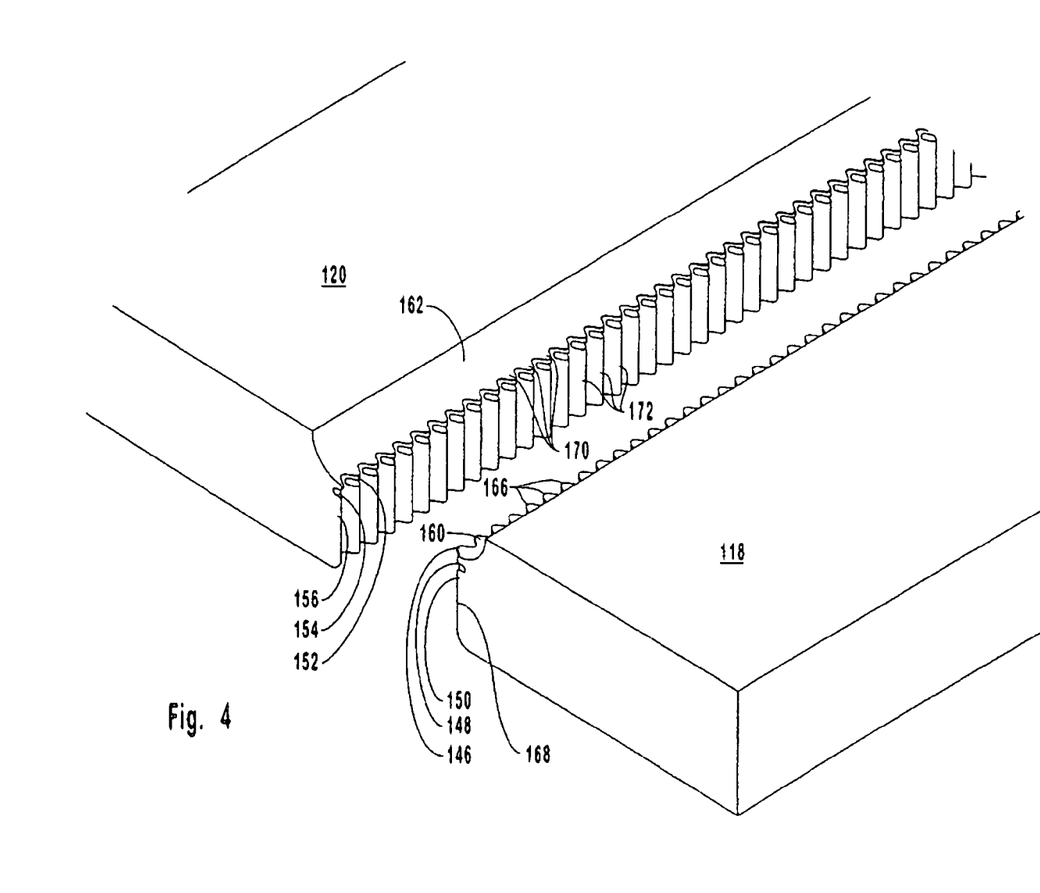
FIG. 4 illustrates a fragmentary perspective view of the clamping assembly according to one embodiment of the present invention, illustrating the clamping assembly in an open position.

With reference to FIG. 4, clamping assembly 114 is shown in further detail. FIG. 4 illustrates first clamping portion 118 and second clamping portion 120 in the open position. First clamping portion 118 includes an upper row 146 of teeth 166 and a lower row 150 of teeth 168 separated by a channel 148 formed therebetween. Similarly, the second clamping portion 120 includes an upper row 152 of teeth 170 and a lower row 156 of teeth 172 separated by a channel 154 formed therebetween. It will be understood that the described upper and lower rows of teeth can be one set of teeth, with a channel formed in the set of teeth. For example, a single set of teeth can be machined on a piece of metal, such as stainless steel, and then a channel subsequently machined or drilled through the teeth to form a distinct upper row 146 and a lower row 150. Thus, it need not be the case to have two different sets of teeth.

Figure 6:
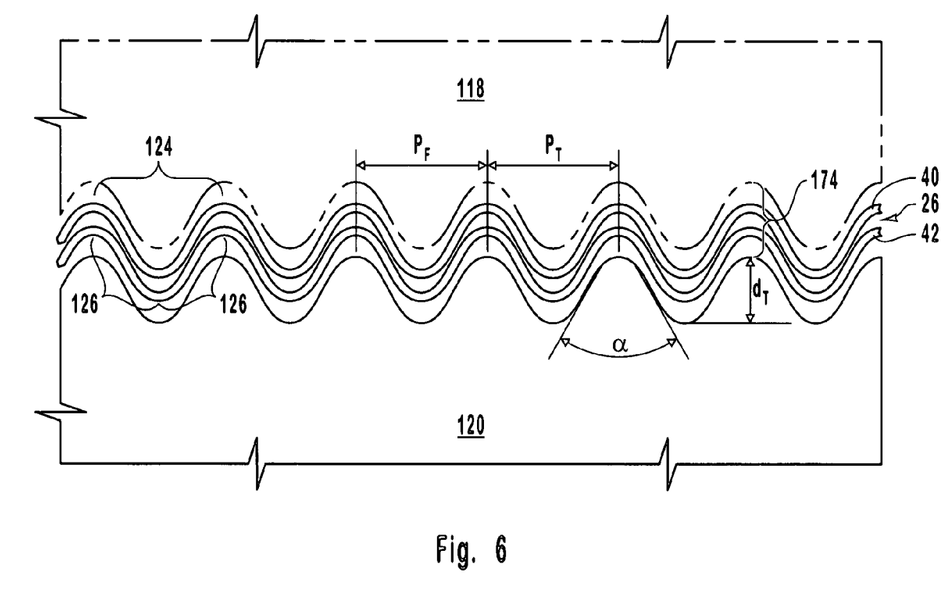
FIG. 6 illustrates a fragmentary top plan view of one clamping portion of the clamping assembly of FIG. 3.

Upper row 146 of teeth 166 on first clamping portion 118 is complementary to upper row 152 of teeth 170 on second clamping portion 120. Similarly, lower row 150 of teeth 168 on first clamping portion 118 are complementary to lower row 156 of teeth 172 on the second clamping portion 120. While the teeth on first clamping portion 118 and second clamping portion are complementary, they may not actually touch each other, leaving a gap 174 therebetween, as shown in FIG. 6. Gap 174 receives a portion of restraining member 26 so that when first clamping portion 118 and second clamping portion 120 are in the closed position, the portion of restraining member 26 is held tightly therebetween. In one embodiment, when clamping portions 118, 120 are in the closed position, gap 174 is from about 24 µm to about 36 µm.

Figure 5:
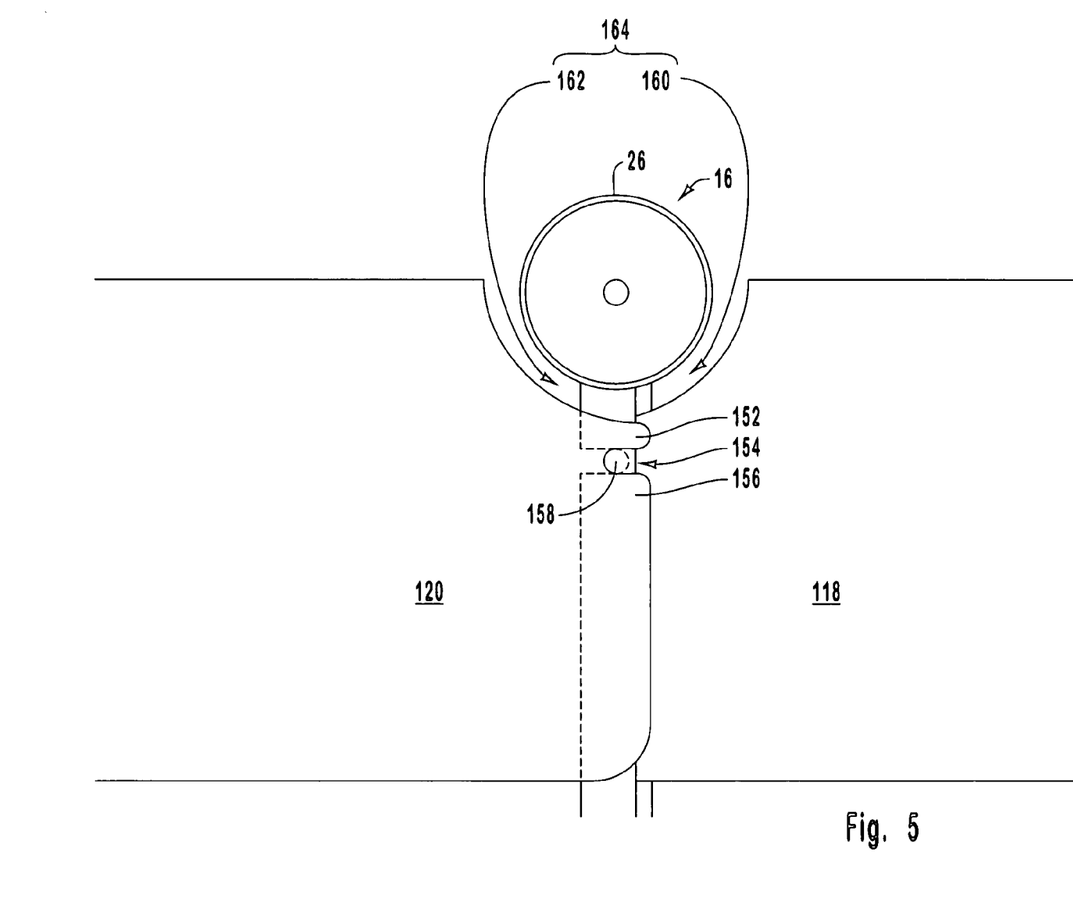
FIG. 5 illustrates a front plan view of the clamping assembly of the present invention.

With reference to FIG. 5, the first channel 148 and second channel 154 combine to form a receiving channel 158 when first clamping portion 118 and second clamping portion 120 are in the closed position. In one embodiment, channels 148, 154 are generally symmetrical in shape. For example, in FIG. 5, the channels 148, 154 combine to form a substantially circular shape receiving channel 158. However, receiving channel 158 may have an oval shape, an ovate shape, a rectangular shape, or any shape which is conducive to the purposes for which the receiving channel is intended, which will be described further below.

In addition, as shown in FIG. 5, first clamping portion 118 includes a first trough portion 160 and second clamping portion 120 includes a second trough portion 162. The first trough portion 160 and second trough portion 162 cooperate to form a combined trough 164 when first clamping portion 118 and second clamping portion 120 are in the closed position. The combined trough 164 is configured to hold part of the medical device during assembly. In another embodiment, not shown, first clamping portion 118 and second clamping portion 120 do not have to include a first trough portion 160 or second trough portion 162. That is, the upper row 146 of teeth 166 and upper row 152 of teeth 170 are formed flush to the top of first clamping portion 118 and second clamping portion 120.

Finally, with respect to clamping assembly 114, first clamping portion 118 and second clamping portion 120 form a gap 176 there under within which a technician can access portions of the restraining device to facilitate assembly of the embolic protection device, as will be discussed in more detail below.

Figure 9:
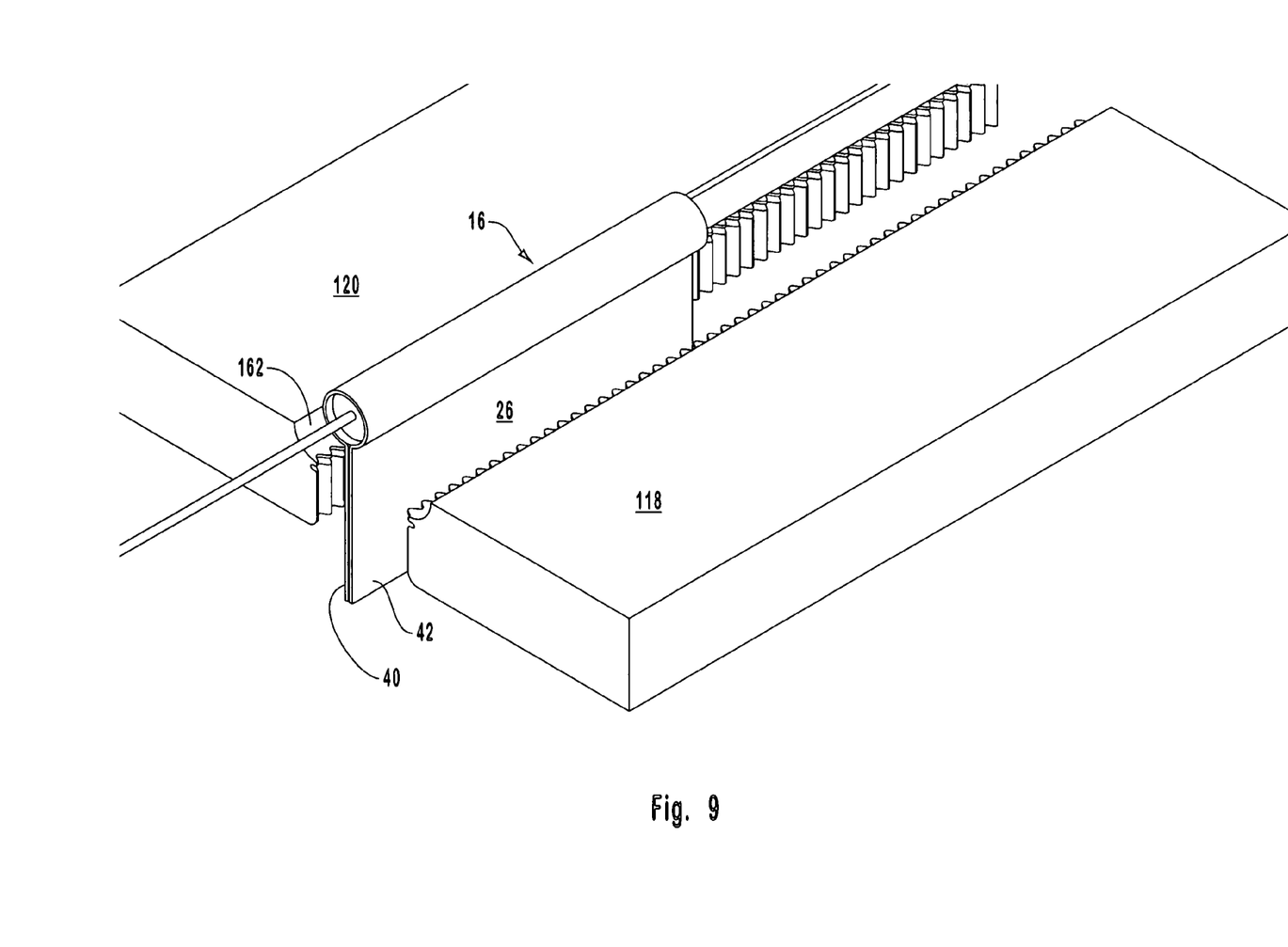
FIG. 9 illustrates the wrapped filter assembly disposed in one clamping portion before stitching of the restraining member.
Figure 10:
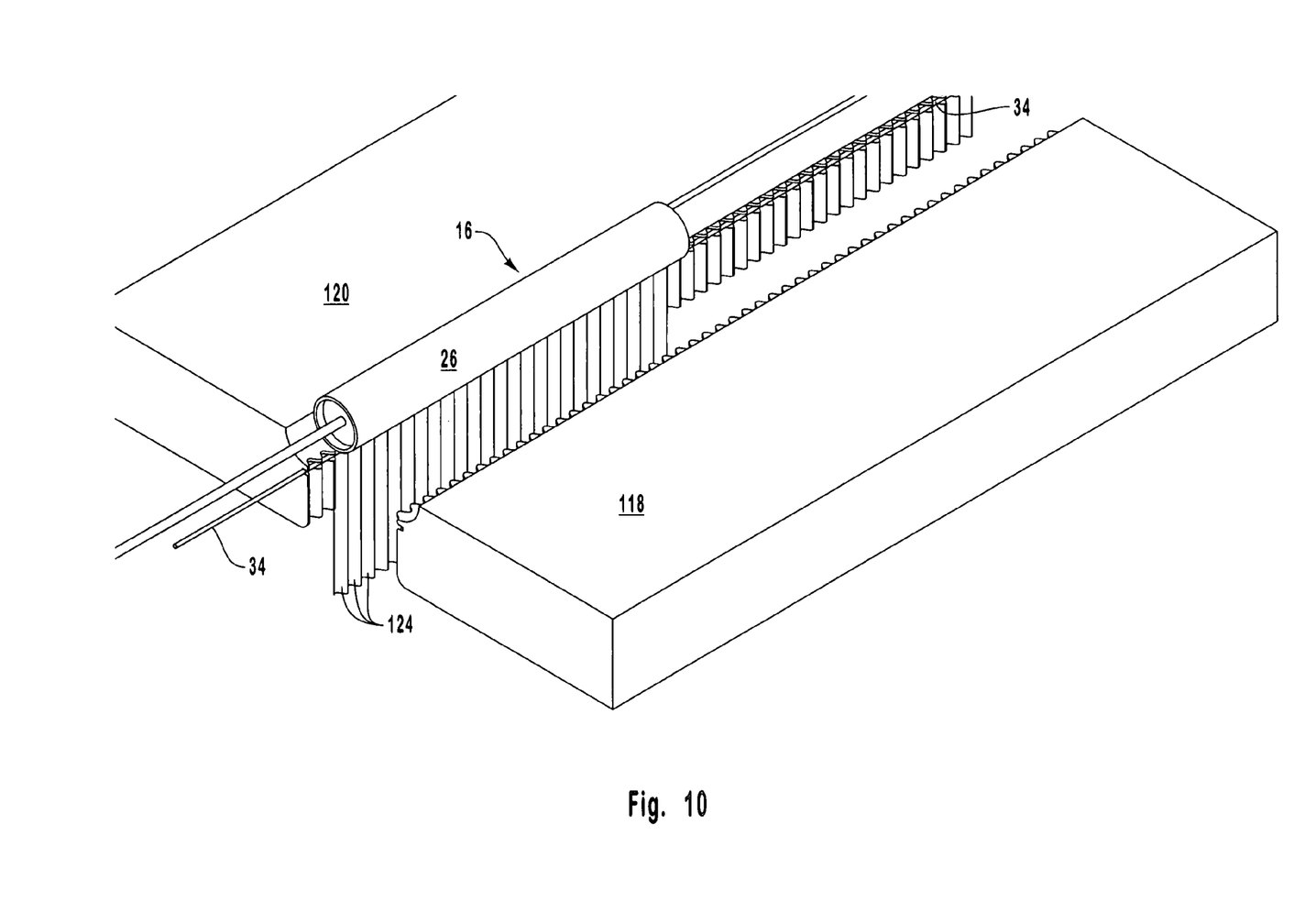
FIG. 10 illustrates the wrapped filter assembly after stitching of the restraining member.

While the method of forming the embolic protection device will be described further below, it is useful to briefly describe the operation of clamping assembly 114. As mentioned above, clamping assembly 114 holds the restraining device 26 in place while securing member 34 is stitched therethrough. As shown in FIG. 9, restraining member 26 is wrapped around filter assembly 16 and sides 40, 42 of the restraining member are placed between clamping portions 118, 120. Teeth 166 of first clamping portion 118 and teeth 170 of second clamping portion 120 clamp sides 40, 42 of restraining member 26 together to cause intermediate portion 44 of the restraining member to be tightly drawn around the packed filter assembly 16. As shown in FIG. 10, first clamping portion 118 and second clamping portion 120 shape sides 40, 42 of restraining member 26 into a folded, accordion-like pattern.

As shown in FIG. 6, any particular fold 124 generally has two contiguous segments 126. Each segment 126 may include (but not necessarily) two layers of restraining member 26 formed by at least a portion of the first side 40 and the second side 42.

In order to place restraining member 26 in as tight of a configuration as possible around filter assembly 16, in one configuration, receiving channel 158 is placed as close to possible to the boundary of the packed filter assembly. Receiving channel 158 provides at least the following functions. First, receiving channel 158 holds restraining member 26 stationary so that securing member 34 can pass through folds 124 of the restraining member. Otherwise, securing member 34 might push restraining member 26 off to the side without penetrating fold 124. Receiving channel 158 also holds segments 126 of folds 124 separate. Otherwise, the thickness of the combined segments 126 of folds 124 might be too thick to be penetrated by an extremely thin securing member 34. In addition, receiving channel 158 provides a taut surface on each segment 126 that is rigid enough to not buckle under the force of securing member 34, but also yielding enough to allow the securing member to penetrate therethrough.

Figure 7A:
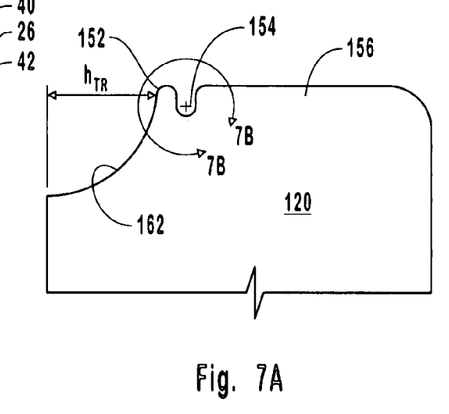
FIG. 7A illustrates a fragmentary front plan view of the clamping portion of FIG. 6.
Figure 7B:
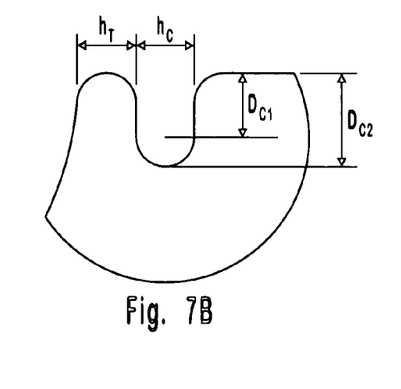
FIG. 7B illustrates a magnified view of the fragmentary front plan view of the clamping portion of FIG. 6.

With reference to FIGS. 6 and 7, dimensions of teeth 166, 168, 170 or 172 will be provided by way of illustration but not by way of limitation. In one embodiment, teeth 166, 168 on first clamping portion 118 have substantially the same dimensions as teeth 170, 172 on second clamping portion 120; but, of course, this may differ. As shown in FIG. 6, in one embodiment, the pitch $p_T$, which is the distance between the same points on adjacent teeth, may be from about 0.015 inches to about 0.050 inches. The depth, $d_T$, of the teeth may be from about 0.007 inches to about 0.050 inches. The angle, $\alpha$, between adjacent teeth 166, is from about 30 degrees to about 80 degrees.

With reference to FIG. 7A, the height, $h_T$, of an upper row of teeth may be from about 75 µm (0.003 inches) to about 1.5 µm (0.006 inches). In one configuration, the height, $h_T$, is as small as possible so as to place the location of the stitch (i.e., securing member 34) as close to the boundary of filter assembly 16 as possible. This provides a tight restraining force and also decreases the profile of the packed embolic protection device 10 so as to increase its ability to navigate through the contours of a patient's vascular system. As illustrated in FIG. 7B, the height of the channel, $h_C$, is from about 50 µm (0.002 inches) to about 225 µm (0.010 inches). The depth, $d_{C1}$, of the channel from the end of teeth 166 to the center of receiving channel 158 is from about 125 µm (0.005 inches) to about 625 µm (0.025 inches). Finally, the height, $h_{TR}$, of the combined trough 164 is from about 250 µm (0.010 inches) to about 1250 µm (0.050 inches). As shown in FIG. 6, the tips of the teeth can be curved or they may be formed with a sharp point.

In addition, as discussed above, first clamping portion 118 and second clamping portion 120 shape sides 40, 42 of restraining member 26 into a plurality of folds 124. As shown in FIG. 6, the pitch, $p_F$, of folds 124 is thus the same as the pitch, $p_T$, of the teeth. The depth, $d_{C2}$, of the teeth must be sufficient so that at least a portion of each fold 124 passes across the opening of receiving channel 158. Furthermore, receiving channel 158 should be sized to take into consideration the existence and size of gap 174. The distance from the channel opening to the center of the receiving channel 158, $d_{C1}$, is generally less than the depth of the channel, $d_{C2}$, However, although not shown in FIG. 7A, the depth of the teeth is generally greater than the depth of the channel, $d_{C2}$. In one embodiment, the depth of the channel, $d_{C2}$, is about half the length of the depth of the teeth, $d_T$.

While a continuous row of upper teeth 166 and lower teeth 168 are shown in the drawings, it is only essential that at least a portion of first clamping portion 118 and second clamping portion 120 include at least some teeth. For example, in one embodiment, a plurality of groups of teeth may be formed along the length of first clamping portion 118 and second clamping portion 120, the groups of teeth being complementary to groups of teeth on the opposing clamping portion.

Figure 8:
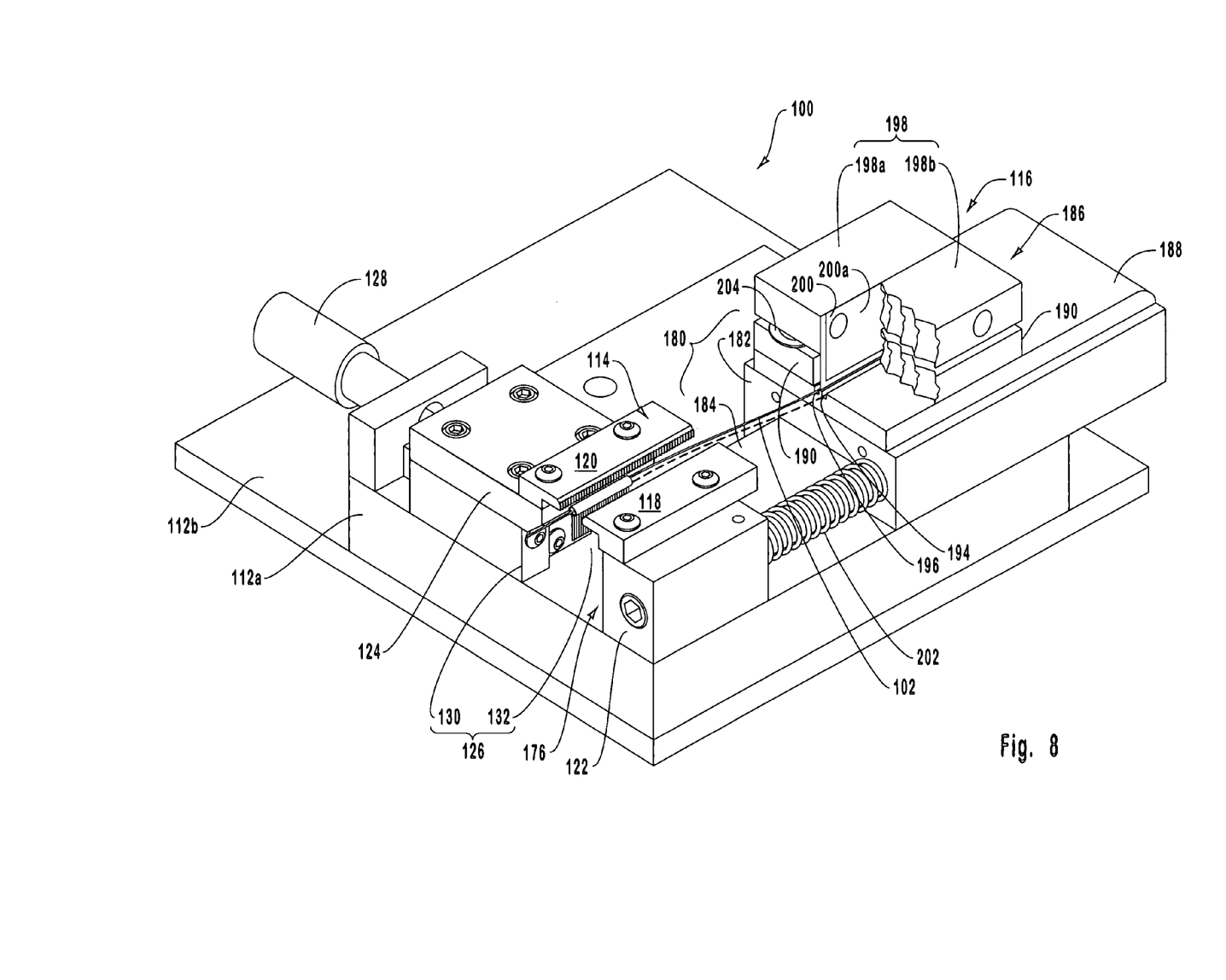
FIG. 8 illustrates a fragmentary perspective view of the clamping assembly and advancing assembly, showing the placement of the guide wire and the securing member during assembly of the embolic protection device.

Turning to FIGS. 3 and 8, advancing assembly 116 which threads or stitches securing member 34 through restraining member 26 will now be discussed in more detail. Advancing assembly 116 includes a linear positioning system 180 which may be similar to linear positioning system 126 discussed above with respect to clamping assembly 114. Linear positioning system 180 allows advancing assembly 116 to be placed in slidable relation to clamping assembly 114. Linear positioning system 180 includes a carriage 182 disposed on a slide 184.

Advancing assembly 116 includes a threading assembly 186 disposed on linear positioning system 180. A spacer block 188 is optionally disposed between threading assembly 186 and linear positioning system 180. Spacer block 188 is provided to align threading assembly 186 with the clamping assembly 116. Thus, spacer block 188 may not be necessary if the carriage 182 is of the right height to form the desired alignment.

Threading assembly 186 includes a pair of guide blocks 190 disposed on spacer block 188. The guide blocks 190 cooperate to form a channel 192 (FIG. 2) therebetween. As such, guide blocks 190 will be collectively referred to hereafter as guide block 190. The bottom surface of the channel 192 (FIG. 2) is thus formed on spacer block 188. Alternatively, guide block 190 and spacer block 188 could be formed integrally to form a single guide block having a channel formed on the top surface thereof. The bottom surface of channel 192 (FIG. 2) includes a central groove 194 and an offset groove 196. The central groove 194 is configured to receive a portion of securing member 34. The offset groove 196 is configured to receive a portion of guide member 102. The central groove 194 and offset groove 196 are spaced apart to prevent securing member 34 and guide wire 102 from crossing or interfering with each other.

Threading assembly 186 further includes an advancement head 198 slidably disposed on guide block 190. Advancement head 198 includes an engagement member 200 extending downwardly therefrom to be disposed in channel 192 of guide block 190. As shown in FIG. 8, in one embodiment, engagement member 200 is a vertical blade 200*a* which is bolted onto a first and second block 198*a*, 198*b*. The first and second block 198*a*, 198*b* form the advancement head 198. In addition, FIG. 8 shows spring washer 204 disposed between the advancement head 198 and guide block 190. Spring washers 204 bias advancement head 198 upward so that engagement member 200 may be disposed in channel 192, but suspended over the bottom surface of the channel.

Threading assembly 186 thus performs an incremental stitching movement as follows: pressure is applied to the top of advancement head 198 to push it downward and forward. Consequently, engagement member 200 moves downward and then forward into central groove 194. At the end of the pushing motion, spring washer 204 lifts advancement head 198 upward and backward, returning it to its original resting position. This, in turn, releases engagement member 200 from contacting central groove 194 and suspends the engagement member there over. It will be appreciated that advancement head 198 may include only a single advancement block 198*a* coupled to the engagement member 200 while still being able to sufficiently perform the stitching motion described herein.

When securing member 34 is disposed in central groove 194, engagement member 200 engages and advances the securing member forward. Because securing member 34 can be extremely thin, the portion of engagement member 200 that contacts the securing member reinforces the length of the securing member so that it does not buckle under the pressure applied thereto. Thus, engagement member 200 provides the dual function of advancing and reinforcing the securing member.

The movement of threading assembly 186 may be automated, for example, by using pneumatic cylinders to push the advancement head 198 down and advance it forward. In another embodiment (not shown), an automatic track may be used to feed securing member 34 forward through an alignment tube. The inner diameter of the alignment tube is substantially similar to the diameter of the securing member. The distal end of the alignment tube is placed against the first fold 124 so that securing member 34 can pass through the alignment tube and penetrate the first fold. In this manner, securing member 34 is reinforced along the length of the alignment tube. Note that this embodiment forms a continuous advancing movement rather than the incremental advancing movement provided by threading assembly 186 shown in FIG. 3.

A biasing spring 202 is disposed between clamping assembly 114 and advancing assembly 116. In particular, biasing spring 202 is connected at one end to carriage 182 and at an opposing end to first clamping base 122. As such, when linear positioning system 180 is released, it can be biased backward, automatically resetting its position so that the operator can simply reload advancing assembly 116 with a new securing member 34.

With reference to FIGS. 9 and 10, the method of assembling embolic protection device 10 using stitching device 100 will now be described in detail. FIG. 9 illustrates restraining member 26 before it is stitched, while FIG. 10 illustrates the restraining device after stitching. Intermediate portion 44 of restraining member 26 is wrapped around filter assembly 16 in such a manner so that filter assembly 16 is packed within the space bounded by restraining member 26, thus forming a wrapped filter assembly 16. Sides 40, 42 of restraining member 26 hang downward and may or may not be equal in length. The wrapped filter assembly 16 is then placed in one of the trough portions 60, 62, if present. The wrapped filter assembly 16 is placed in a clamping portion that is stationary, if present, so that the opposing clamping portion can be incrementally brought into contact with sides 40, 42 of restraining member 26.

Gap 176 formed beneath first clamping portion 118 and second clamping portion 120 allows a technician to reach therein with their fingers or a grasping tool (e.g., tweezers) and draw sides 40, 42 of restraining member 26 downward into gap 176. As clamping portions 118, 120 begin to engage restraining member 26, sides 40, 42 of the restraining member can be further drawn downward to tighten the restraining member around the packed filter assembly 16. This is repeated until the desired tightness is achieved around filter assembly 16. At the same time, sides 40, 42 of restraining member 26 are being placed into a plurality of folds 124 by the clamping force of first clamping portion 118 and second clamping portion 120.

With reference to FIG. 10, folds 124 of restraining member 26 are held together and restrained in their folded configuration by securing member 34 which is threaded or forced through receiving channel 158 when first clamping portion 118 and second clamping portion 120 are in the closed position. Advancing assembly 116 threads securing member 34 through folds 124 of restraining member 26. Prior to, simultaneously with, or subsequently to clamping restraining member 26 in clamping assembly 114, securing member 34 is placed in central groove 194 of channel 192 formed in guide block 190. As discussed above, advancing assembly 116 should be designed so that when securing member 34 is placed in central groove 194, the securing member aligns centrally with receiving channel 158 of clamping assembly 114. Advancing assembly 116 may then be moved forward until the distal end of securing member 34 is centrally disposed in receiving channel 158 and contacts the first segment 126 of the first fold 124.

Threading assembly 186 may be fully assembled or partially assembled during placement of securing member 34 in channel 192. If not fully assembled, advancement head 198 is positioned over guide block 190 such that engagement member 200 (i.e., blade 200*a*) is disposed directly over central groove 194. If fully assembled, engagement member 200 may already be disposed in channel 192 directly above central groove 194.

Threading assembly 186 is then operated by the technician. Pressure is applied to the top of advancement head 198 to push it downward and forward. Consequently, engagement member 200 moves downward into central groove 194 to contact at least a portion of securing member 34 disposed in the central groove. The pushing action advances securing member 34 forward in central groove 194. At the end of the pushing motion, spring washer 204 lifts advancement head 198 upward and backward, returning it to its original resting position. This, in turn, releases engagement member 200 from contacting securing member 34. In this manner, securing member 34 can be incrementally advanced forward with enough force to cause it to penetrate the folds of restraining member 26. Securing member 34 is threaded through the longitudinal direction of embolic protection device 10, thus forming a seam 46 (FIG. 2). As shown in FIG. 10, when first clamping portion 118 and second clamping portion 120 are opened, embolic protection device 10 is released with restraining member 26 held together by securing member 34.

Guide member 102 (FIGS. 1 and 2) can be removed after wrapping filter assembly 16 but before stitching of the restraining member, or it may be removed after stitching of the restraining member.

When the stitched filter assembly 16 is removed from clamping assembly 114, the clamping force is removed from folds 124 which may cause them to relax. This, in turn, may affect securing member 34 to cause it to bend. In fact, the compliancy and tensile strength of restraining member 26 may bias seam 46 to straighten when the stitched filter assembly 16 is removed from clamping assembly 114.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the cliams are to be embraced within their scope.

What is claimed is:

1. A method for securing a restraining member about a portion of a medical device, the restraining member configured to be selectively removed from the medical device during deployment of the medical device, the method comprising:
   wrapping the restraining member around a portion of the medical device;
   clamping the restraining member so as to form one or more folds in the restraining member; and
   advancing a securing member through at least some of the one or more folds.

2. The method as recited in claim 1, further comprising drawing downward one or more end portions of the restraining member so as to tighten an intermediate portion of the restraining member around the portion of the medical device.

3. The method as recited in claim 1, further comprising reinforcing the area of the one or more folds through which the securing member penetrates.

4. The method as recited in claim 1, further comprising incrementally advancing the securing member.

5. The method as recited in claim 4, further comprising reinforcing at least a portion of the securing member as the securing member is advanced.

6. The method as recited in claim 1, further comprising continuously advancing the securing member.

7. A method for securing a restraining member about a portion of a medical device, the restraining member configured to be selectively removed from the medical device during deployment of the medical device, the method comprising:
   at least partially surrounding a portion of the medical device with the restraining member;
   creating one or more folds in the restraining member while securely holding the restraining member; and
   advancing a securing member through at least some of the one or more folds.

8. The method as recited in claim 7, wherein creating one or more folds comprises clamping at least two separate portions of the restraining member with a clamping assembly.

9. The method as recited in claim 7, wherein creating one or more folds comprises:
   locating at least two portions of the restraining member between a first clamping portion and a second clamping portion;
   moving at least one of the first clamping portion and the second clamping portion until the restraining member is securely retained by the first clamping portion and the second clamping portion.

10. The methods as recited in claim 7, further comprising mounting the securing member within a central groove of an advancing assembly.

11. The method as recited in claim 7, further comprising mounting a portion of the medical device within an offset groove of an advancing assembly.

12. The method as recited in claim 11, further comprising incrementally advancing the securing member into the restraining member by manipulating the advancing assembly.

* * * * *